United States Patent [19]

Snyder et al.

[11] Patent Number: 5,405,432
[45] Date of Patent: Apr. 11, 1995

[54] CAPILLARY COLUMN METHOD TRANSLATION

[75] Inventors: Warren D. Snyder, West Chester, Pa.; Leonid M. Blumberg, Hockessin, Del.

[73] Assignee: Hewlett-Packard Company, Palo Alto, Calif.

[21] Appl. No.: 108,872

[22] Filed: Aug. 18, 1993

Related U.S. Application Data

[63] Continuation of Ser. No. 883,995, May 18, 1992, abandoned.

[51] Int. Cl.⁶ ............................................. B01D 15/08
[52] U.S. Cl. ............................................. 95/82; 95/87
[58] Field of Search ................................. 95/82–89; 96/101–103

[56] References Cited

U.S. PATENT DOCUMENTS

| | | | |
|---|---|---|---|
| 3,581,465 | 6/1971 | Haruki et al. | 55/67 |
| 4,824,446 | 4/1989 | Mowery, Jr. | 55/386 X |
| 4,927,532 | 5/1990 | Pospisil et al. | 55/386 X |
| 4,994,096 | 2/1991 | Klein et al. | 55/67 X |
| 5,032,151 | 7/1991 | Klein et al. | 55/67 X |
| 5,094,741 | 3/1992 | Frank et al. | 55/386 X |
| 5,108,466 | 4/1992 | Klein et al. | 55/67 X |
| 5,133,859 | 7/1992 | Frank et al. | 55/386 X |
| 5,141,532 | 8/1992 | Sacks et al. | 55/67 |

FOREIGN PATENT DOCUMENTS

| | | | |
|---|---|---|---|
| 60-073457 | 4/1985 | Japan | 55/67 |
| 0608095 | 5/1978 | U.S.S.R. | 55/67 |

OTHER PUBLICATIONS

Giddings, J. C., "Optimum Conditions for Separation in Gas Chromatography", *Analytical Chemistry*, vol. 32, No. 12, Nov. 1960, pp. 1707–1711.

*Primary Examiner*—Robert Spitzer
*Attorney, Agent, or Firm*—Richard F. Schuette

[57] ABSTRACT

The invention is a method for modifying a known chromatographic method without changing peak elution order and with little or no change in resolution. Column and operational parameters of a known method are systematically translated to ensure that a new chromatographic method having possibly different column and operational parameters has a chromatographic output with similar separation.

5 Claims, 6 Drawing Sheets

STEP 1: CALCULATE FOR COLUMN 1

$$u_{01} = \frac{\pi (P_{i1}^2 - P_{01}^2) r_1^2}{16 \eta_1 l_1 P_{01}}$$

$$j_1 = \frac{3}{2} \frac{(\bar{P}_1^2 - 1)}{(\bar{P}_1^3 - 1)}$$

$$\bar{U}_1 = j U_{01}$$

$$t_{m1} = 1/\bar{U}_1$$

STEP 2: INPUT FOR COLUMN 2:
 length ($l_2$)
 diameter ($d_2$)
 film thickness ($d_{f2}$)
 carrier gas type STEP 3: CALCULATE $r_l$, $r_d$, $r_{df}$, $r_\beta$, $r_\eta$
 TWO CASES:
  [1] COLUMN 2 = COLUMN 1; LET $r_u = 3$
  [2] COLUMN 2 = COLUMN 1; LET $r_u = 1/r_d$

STEP 4: TRANSLATE TO COLUMN 2

$$P_{i2}^2 - P_{o2}^2 = \frac{r_\eta r_e r_{uo}}{r_d^2} (P_{i1}^2 - P_{o1}^2)$$

$$\frac{r_t}{r_\beta} = \frac{r_e r_{df}}{r_j r_{uo} r_d}$$

FROM WHICH WE FIND $P_{i2}$, $u_{o2}$, $u_2$ AND $t_{m2}$ FOR COLUMN 2

STEP 5: CALCULATE COLUMN 2 OVEN PROGRAM $$t_{i2} = (t_{i1} + t_{m1}) r_t / r_\beta + t_{mz}$$

$$R_{n2} = R_{n1} \cdot \frac{r_\beta}{r_t}$$

$$t_{f2} = t_{f1} \cdot \frac{r_t}{r_\beta}$$

SPEED GAIN = RUNTIME1/RUNTIME2

CAPILLARY COLUMN METHOD TRANSLATION

CROSS REFERENCE TO RELATED APPLICATION

This application is a continuation of Ser. No. 07/883,995, filed on May 18, 1992, and now abandoned.

FIELD OF THE INVENTION

The invention provides a technique for automatically translating and reconfiguring the operating parameters of a gas chromatograph to provide equivalent chromatographic outputs when the column parameters of a chromatographic method are changed.

BACKGROUND OF THE INVENTION

Gas chromatography includes three basic stages; an injection stage where a sample is injected into a separation column located within a gas chromatograph, a separation stage in which a pressurized carrier gas forces the sample to flow through the column and is then separated by the interaction between the sample and a liquid phase bound to the inner walls of the column, and a detection stage where the elution from the column of the separated sample is ascertained. The separation stage is relatively long, and may take twenty minutes or more for the separation of very complex molecules. It is known that increasing flow rate and/or temperature within the gas chromatograph decreases the amount of time required to separate a sample, however such action may reduce efficiency and resolution of the chromatography.

Figure 1:
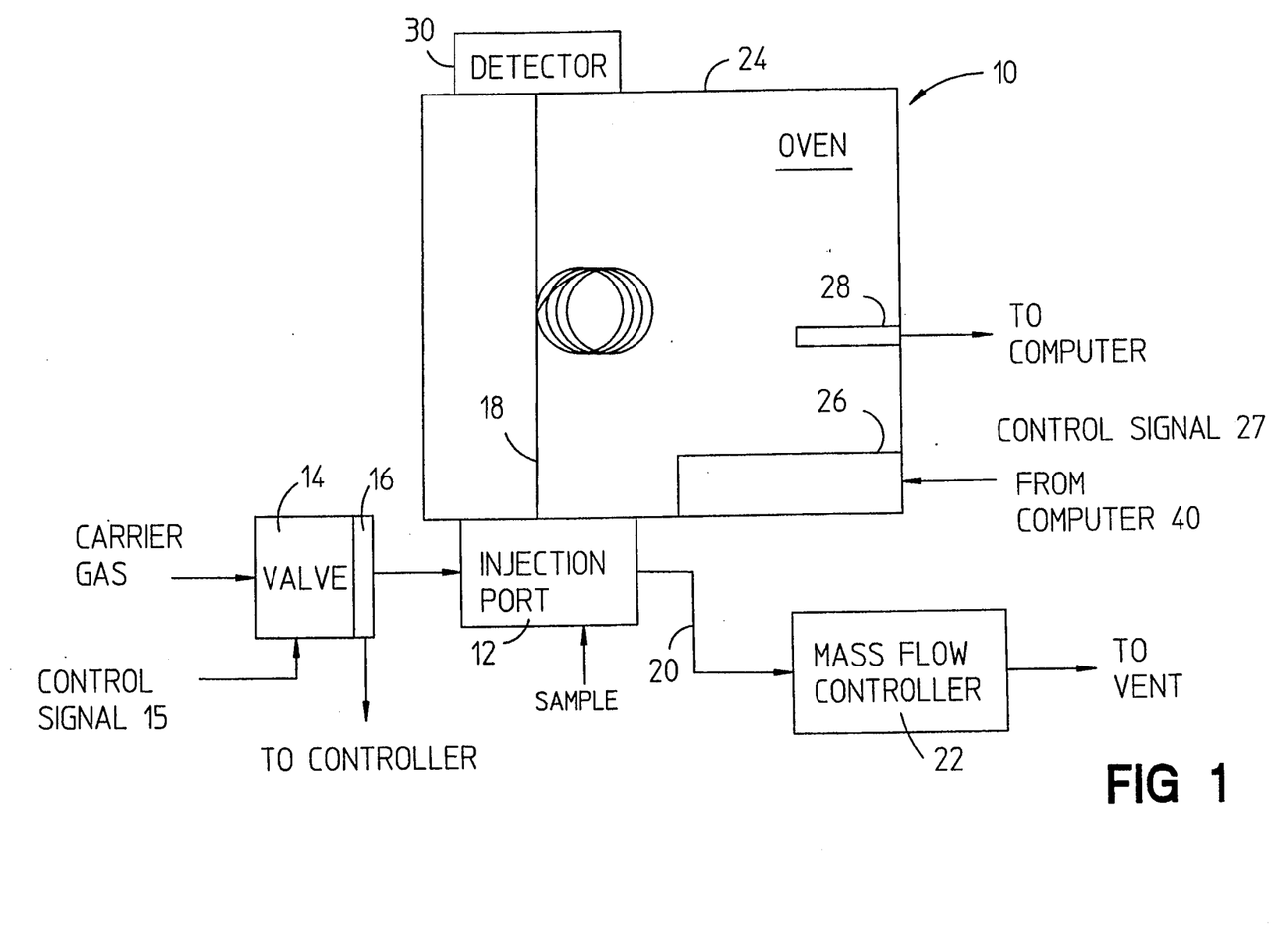
FIG. 1 is an illustration of a typical gas chromatograph having an integrated pressure programmer.
Figure 2:
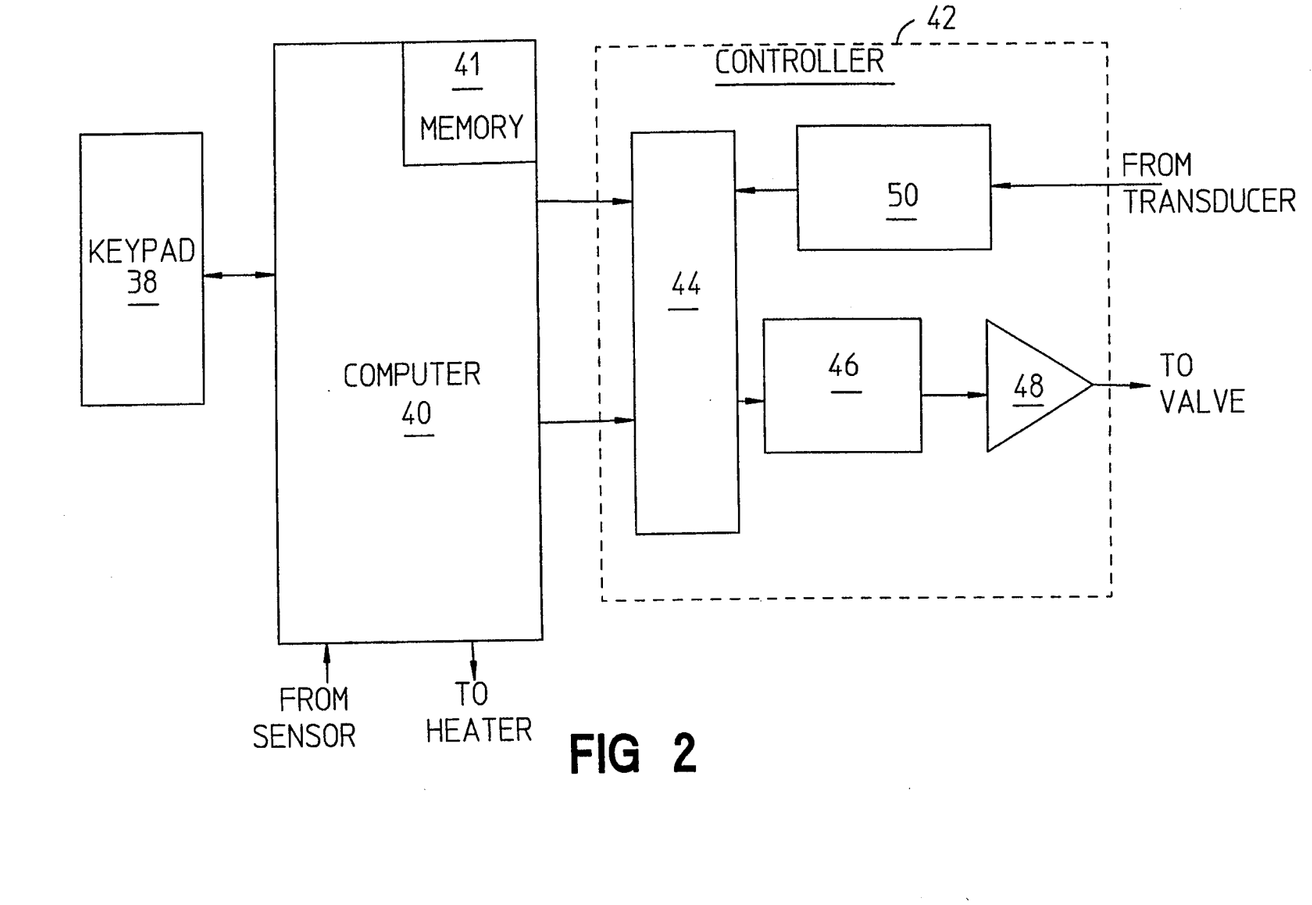
FIG. 2 is a block diagram of the control system of the GC in FIG. 1.

U.S. Pat. No. 4,994,096 discloses how efficiency and resolution can be enhanced by regulating the flow rate and temperature in accordance to the mass flow rate of the carrier gas. FIG. 1 illustrates a gas chromatograph 10 having an integrated pressure programmer and includes a column 18 positioned within oven 24. In order to perform a chromatographic separation of a given sample compound, the sample is injected into a pressurized carrier gas by means of an injection port 12. Valve 14 serves to control the pressure of the carrier gas in response to a control signal 15. A pressure transducer 16 generates a pressure information signal representative of the carrier gas provided to injection port 12. A heating unit 26 provides heat to the oven in response to a control signal 27 and a temperature sensor 28 generated by a computer 40. The carrier gas/sample combination passing through column 18 is exposed to a temperature profile resulting from the operation of the heater 26 within oven 24. Mass flow controller 22 is employed for controlling the amount of carrier provided to the column 18. As components exit column 18, they are detected by detector 30. FIG. 2 illustrates the electronic controls including keypad 38, computer 40 and controller 42. Computer 40 includes a central processing unit and all associated peripheral devices, such as random access memories, read-only memories, input/output isolation devices, clocks and other related electronic components.

Figure 3:
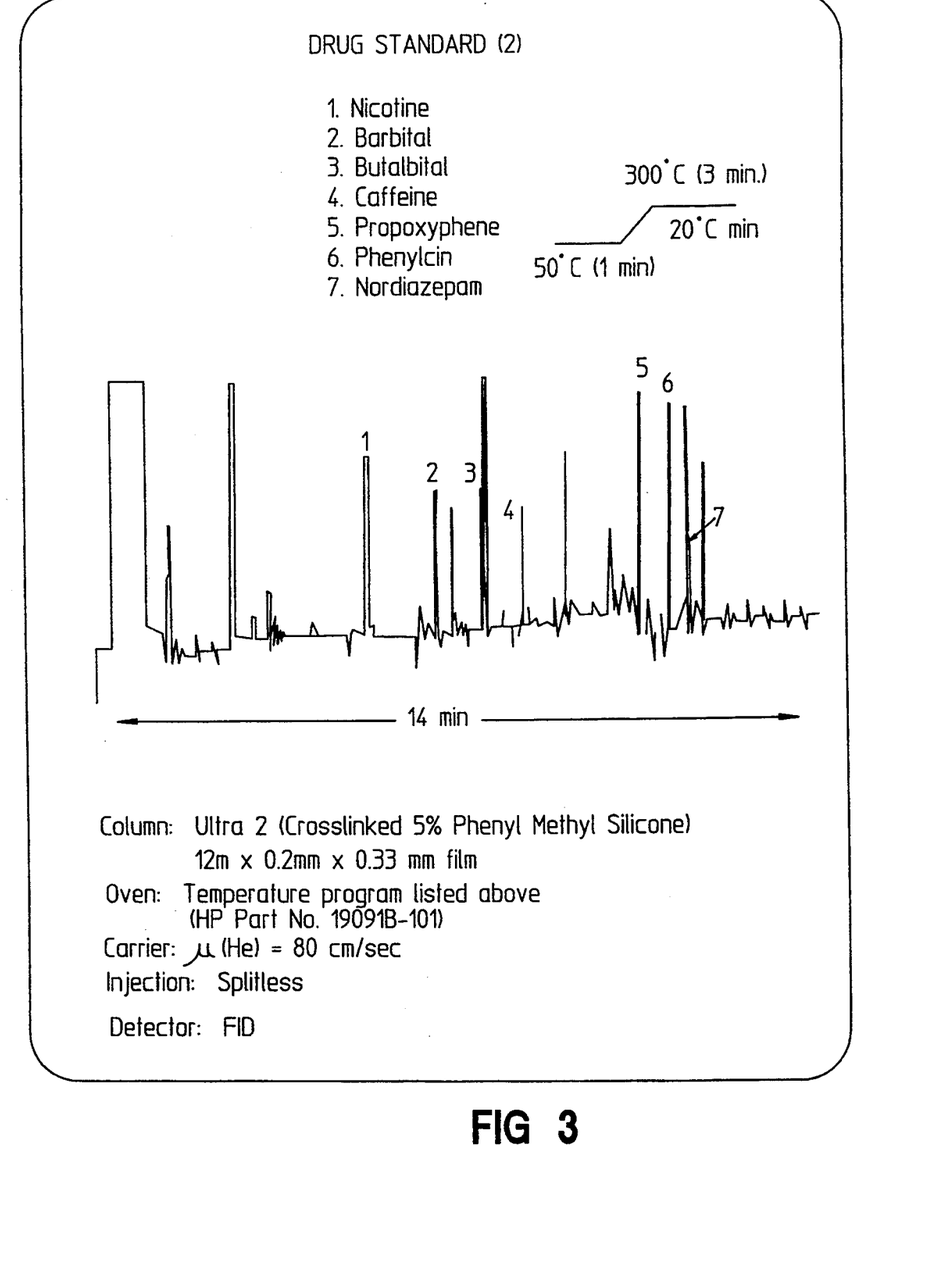
FIG. 3 illustrates the chromatographic output of a known capillary column method entitled "Drug Standard (2)".

An analyst attempting to separate and identify certain compounds typically refers to compilations of chromatographic methods to obtain a method which has the greatest potential for separating and identifying certain compounds. One such compilation is entitled "Analytical Solutions—a Collection of Chromatograms from Hewlett-Packard". This compilation contains a collection of over 400 capillary column chromatographic methods developed by a variety of Hewlett-Packard field and factory personnel over a period of ten years. FIG. 3 illustrates one chromatographic method entitled "Drug Standard (2)" which is employed for identifying known drugs and highlights which column parameters and which operating parameters are required to replicate this method. Column parameters include: column length (l), column inside diameter (d) and stationary phase (thickness ($d_f$) and type). Operating parameters include: carrier gas (type, pressure and/or flow rate) and oven temperature (including program ramp rates). A sample chromatogram highlighting the time at which known compounds will elute from the column is also illustrated, thus making it possible to tentatively identify these compounds based on elution order and time.

It is generally not possible to change only one of the column or operating parameters without affecting the elution time of a given compound, resolution and in many cases the elution order. However, the vast number of column types and sizes makes it quite conceivable that an analyst may be unable to practice a published method for lack of a specified column size. Therefore, an analyst may wish to modify a method to work with a column not specified in a desired chromatographic method, or use smaller columns to increase the speed of separation or larger columns to increase sample capacity. Such modifications require a tremendous amount of time to implement as chromatographic theory, intuition and empirical experimentation are required to ascertain new operating parameters which will provide substantially the same chromatographic output as with the existing column. Once the new operating parameters are ascertained, they must be manually inputted into the gas chromatograph. Again, once a method has been developed, it is generally not possible to change any of the column or operating parameters without changing the chromatographic output.

It is generally known that the speed of a chromatographic process is inversely proportional to the resolution. When the chromatographic output contains well resolved peaks, it is possible to make a tradeoff between speed and resolution. Faster analysis time in a chromatographic process may be accomplished by implementing one or more of the following: a shorter column, a column with a smaller inside diameter (i.d.), a thinner liquid phase film, a faster temperature program rate, or a higher carrier gas linear velocity. An analyst will typically first try changing the temperature program rate and/or the carrier gas velocity. Since the magnitude of the change is determined empirically, there is no quantitative way of achieving a calculated change in speed. Additionally, such a change will typically affect the chromatographic output.

It is known that smaller diameter columns provide for faster chromatography, however, smaller columns also require smaller injected sample sizes, as well as injectors, inlets and detectors which have a correspondingly faster rate. It is therefore desirable to translate a known chromatographic method to provide for reduced sample sizes such that improved speed (decreased runtime) can be achieved without changing the elution order or resolution.

SUMMARY OF THE INVENTION

The invention provides for the development of a method and apparatus for predictably translating known chromatographic methods where the existing column is replaced with a new column having different parameters such that there is little or no loss in resolution. In particular, the invention provides for quantitatively changing existing column and/or existing operational parameters of a gas chromatograph as set forth in a known chromatographic method to provide a modified chromatographic method having possibly different column and operational parameters but a chromatographic output with similar separation.

System software controls the gas chromatograph to automatically reconfigure with new operational parameters in response to the analyst inputting new column parameters corresponding to a new column. The existing column and operating parameters are stored in the gas chromatograph such that upon input of the new column parameters, system software has all of the information necessary to perform translation calculations to obtain new operating parameters. Once the new operating parameters are calculated, the gas chromatograph is automatically reconfigured with these parameters such that the chromatographic output of the gas chromatograph with the new column and operating parameters is substantially the same as with the old column and old operating parameters.

To maintain constant resolution and the same separation from the existing column to the new column requires that they contain the same number of theoretical plates. This is true if the ratio of their lengths and film thicknesses is the same as the ratio of their diameters. Under these conditions, the liquid phase type, the phase ratio ($\beta$) must remain constant. Additionally, the oven temperature program ramp rates are modified such that the temperature at which a given peak will elute from the new column is the same as for the existing column.

Figure 4:
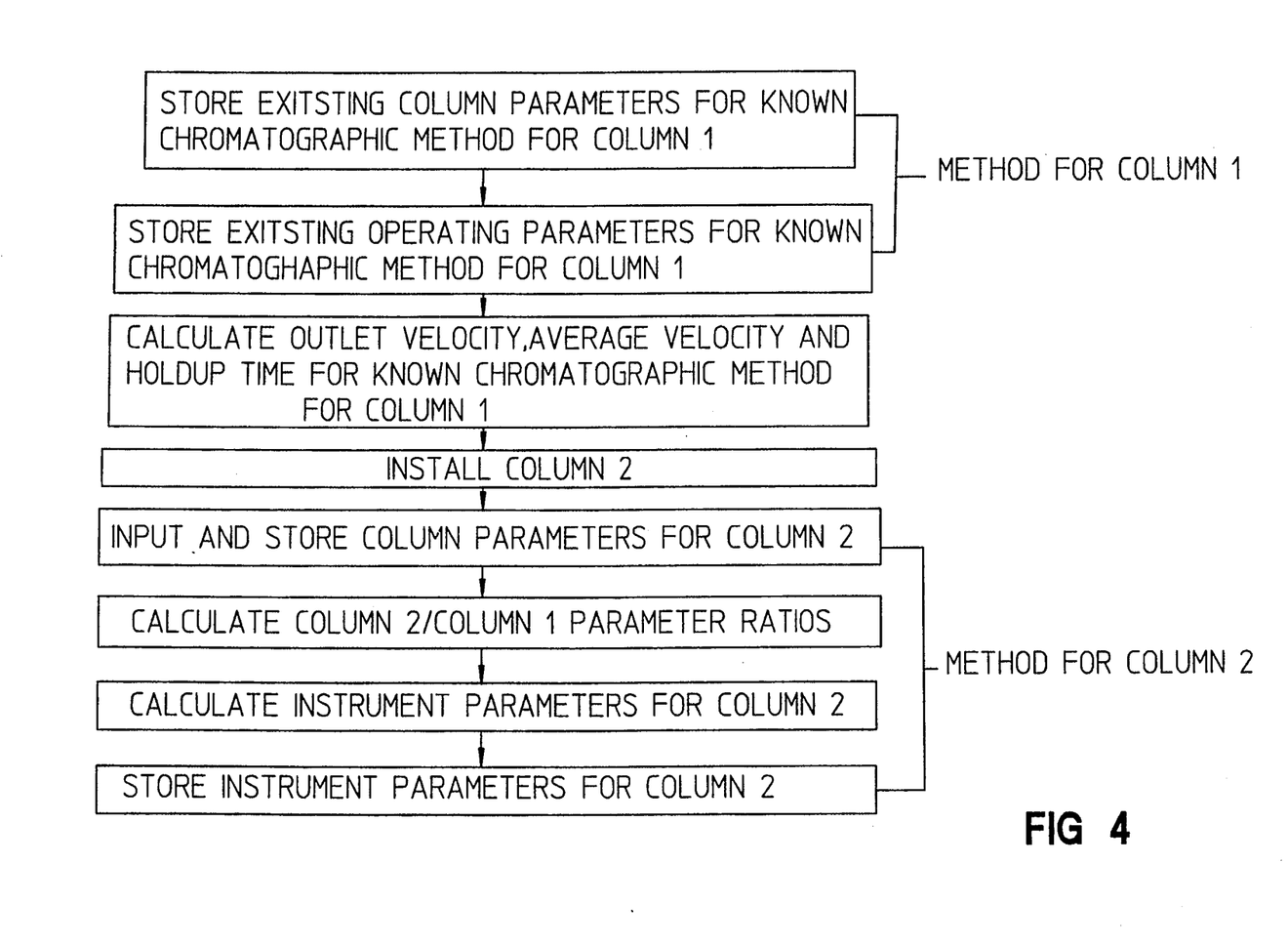
FIG. 4 shows a block diagram illustrating a flow chart highlighting the invention.

The invention translates an existing method into a modified method having the same chromatographic output by compensating for the effects of changes in column and operating parameters. In particular, a chromatographic process can be represented as a number of complex chromatographic equations having column and operating parameters as variables. The invention provides a method and apparatus for automatically updating the operational parameters of a gas chromatograph with a modified method generated by solving these chromatographic equations simultaneously once the new column and/or new operating parameters are ascertained. The invention contemplates that the column outlet linear velocity ($u_{out}$), instead of the more commonly used average linear velocity (u), is employed to determine the required inlet pressure for the new column. This greatly simplifies the calculations which represent the chromatographic process to the point where they can be performed automatically by system software associated with the gas chromatograph. As illustrated in FIG. 4, the inventive method comprises the steps of:

1) storing existing column and operating parameters of the known chromatographic method on column 1; and
2) Calculate outlet velocity, average velocity and holdup time for known chromatographic method on column 1
3) install new column (column 2); and
4) input new column parameters; and
5) calculate column 2/column 1 parameter ratios; and
6) calculate new operating parameters from the parameter ratios; and
7) automatically reconfiguring the gas chromatograph with the calculated new operating parameters such that the chromatographic output of the gas chromatograph with the new column is substantially the same as with the existing column.

The preferred embodiment of the invention provides for system software running in conjunction with the gas chromatograph which has the capability of performing calculations based on the stored chromatographic equations required to translate existing column parameters and existing operating parameters into new column parameters and new operating parameters such that the gas chromatograph can be automatically reconfigured to provide a new output which is equivalent to the output of the known method with the new column.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DESCRIPTION OF THE PREFERRED EMBODIMENT

FIG.4 is a block diagram of the inventive method and apparatus in which existing column and operating parameters of a known chromatographic method are employed for translating new operating parameters when a new column having new column parameters is installed. Once the new column parameters are stored in the gas chromatograph, new operating parameters are calculated and automatically stored in system software running on the gas chromatograph. The system software controls the gas chromatograph such that the chromatographic output with the new column is the same as with the known chromatographic method having different column and operating parameters.

The following definitions for column and operational parameters are stored in the system software of the gas chromatograph and are used for proper translation.

---

Column Parameters (wherein a subscript 1 refers to column 1 and a subscript 2 refers to column 2):

-continued $l_1$ = length
$d_1$ = inside diameter
$d_{f1}$ = film thickness

Operational Parameters:

$P_{i1}$ = inlet pressure
$P_o$ = outlet pressure
$j$ = James-Martin pressure correction
$B$ = phase ratio = $d/4d_f$ for thin films
$u_o$ = outlet linear velocity
$\bar{u}$ = average linear velocity
$\bar{p}$ = $P_i/P_o$
$t_m$ = holdup time
$t_r$ = retention time
$t_r'$ = $t_r - t_m$ = corrected retention time
$F_o$ = outlet flow
$n$ = carrier gas viscosity Oven Program Par.:

$T_i$ = initial temp
$t_i$ = initial time
$R_1$ = ramp rate 1
$T_{f1}$ = final temp 1
$t_{f1}$ = final time 1
$R_2$ = ramp rate 2

$T_{f2}$ = final temp 2

$t_{f2}$ = final time 2

. . . .
. . . .
. . . .

$t_{fn}$ = nth final time (Note that for isothermal, $R_1 = 0$, $T_i$ = isothermal temp)
Sample Parameters: v = Sample volume injected
Split Ratio = $\dfrac{\text{Split Vent Flow}}{F_o}$ For an additional understanding of these terms, a publication entitled "A Standard Practice for Gas Chromatograph Terms and Relationships" is attached as an appendix.

Expressions

The following expressions are written as ratios of column 2 to column 1 parameters, e.g.:

$$r_1 = \frac{\text{length col 2}}{\text{length col 1}} = \frac{l_2}{l_1}$$

Expressions $$r_l = \frac{l_2}{l_1}$$

$$r_d = \frac{d_2}{d_1}$$

$$r_{df} = \frac{d_{f2}}{d_{f1}}$$

$$r_\beta = \frac{\beta_2}{\beta_1} = \frac{r_d}{r_{df}}$$

$$r_R = \text{resolution ratio} = \frac{\sqrt{N_2}}{N_1}$$

$$r_P = \frac{P_{i2}^2 - P_o^2}{P_{i1}^2 - P_o^2} = \frac{r_\eta \, r_l \, r_{uo}}{r_d^2}$$

$$r_j = \frac{j_2}{j_1} = \frac{(\overline{P_2}^2 - 1)(\overline{P_1}^3 - 1)}{(\overline{P_2}^3 - 1)(\overline{P_1}^2 - 1)}$$

-continued $$r_t = \frac{t_{m2}}{t_{m1}} = \frac{r_l}{r_j \, r_{uo}}$$

$$r_{uo} = \frac{u_{o2}}{u_{o1}}$$

$$\frac{r_t}{r_\beta} = \frac{r_l \, r_{df}}{r_j \, r_{uo} \, r_d}$$

$$r_{tR'} = \frac{t_{R2}'}{t_{R1}'} = \frac{r_t}{r_\beta}$$

$$r_v = \frac{v_2}{v_1} = r_d \, r_{df} \, r_l$$

$$r_u = \frac{\bar{u}_2}{\bar{u}_1} = \frac{j_2 \, u_{o2}}{j_1 \, u_{o1}} = r_j \, r_{uo}$$

$$r_{Fo} = \frac{F_{o2}}{F_{o1}} = r_d^2 \, r_{uo}$$

$$r_\eta = \frac{\eta_2}{\eta_1}$$

Additional Expressions

Poiseuille's equation for flow of a compressible fluid in a capillary:

$$F_o = \frac{\pi(P_i^2 - P_o^2)r^4}{16\eta l P_o} = \pi r^2 u_o$$

James-Martin correction factor:

$$j = \frac{3(\overline{P}^2 - 1)}{2(\overline{P}^3 - 1)}$$

$$\bar{u} = j u_o = \frac{l}{t_m}$$

Poiseuille's equation gives the outlet flow or linear velocity from a capillary column as a function of inlet and outlet pressure of a given type of carrier gas at a given temperature (temperature affects the viscosity of the gas $\eta$ plus the column parameters length, and internal diameter or radius.

Figure 5:
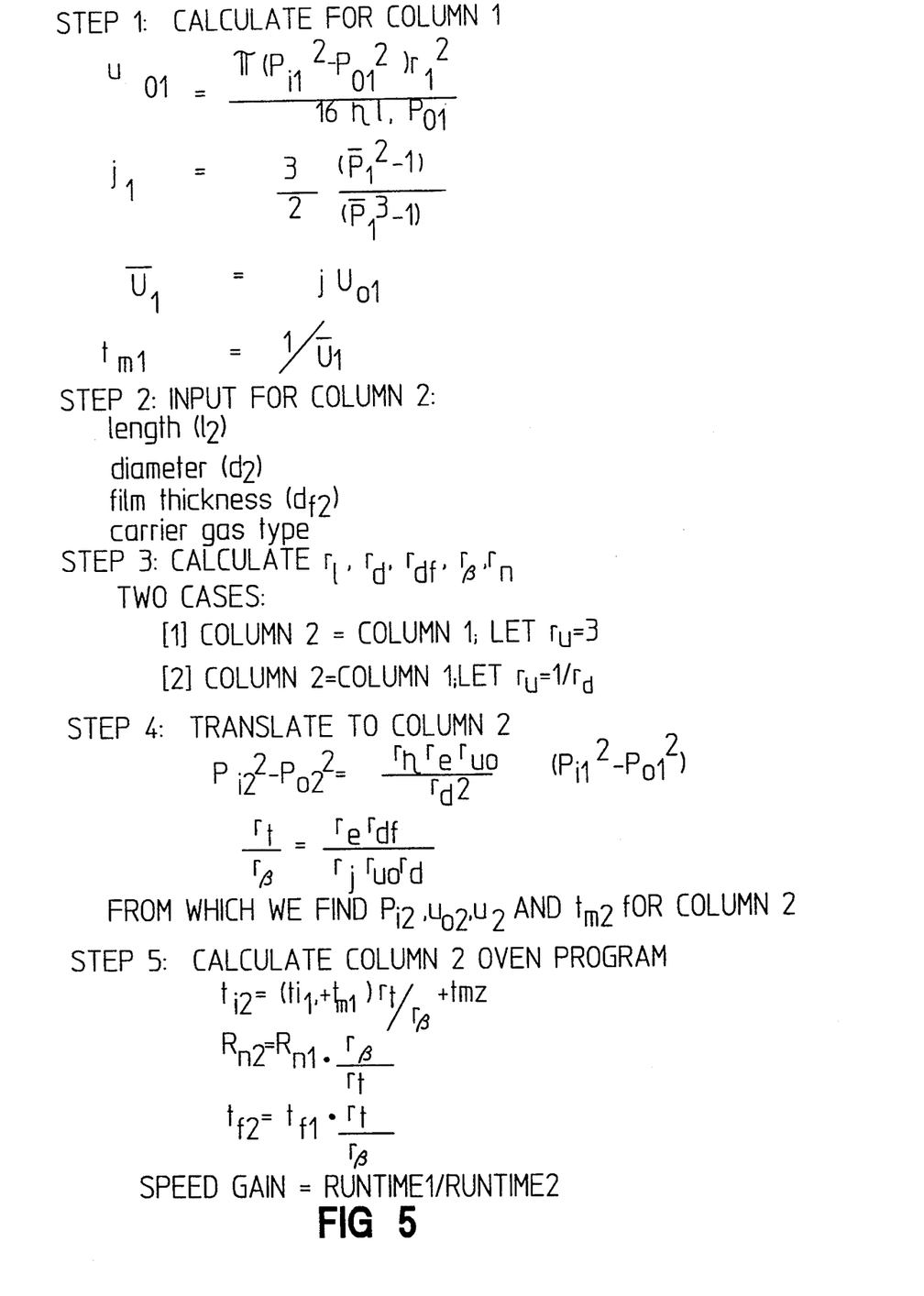
FIG. 5 shows a block diagram illustrating a flow chart highlighting the step of calculating new operating parameters.
Figure 6A:
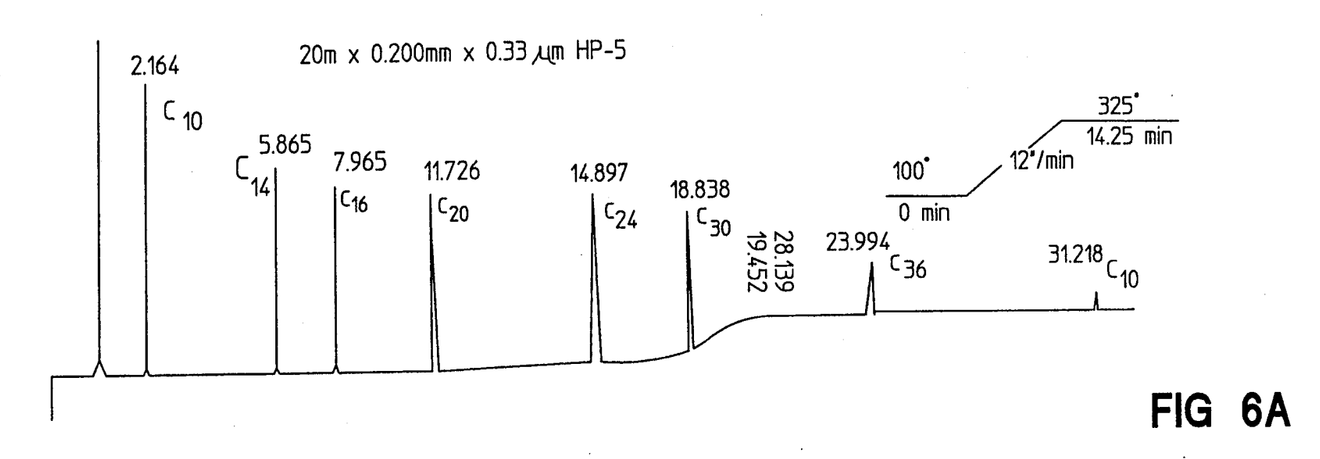
FIG. 6A illustrates the chromatographic output of a gas chromatograph which employs "existing" column parameters and "existing" operating parameters (8.95 psig $H_2$, $u_o$=50 cm/sec, u=38 cm/sec, 0.5 ul split 275:1, chart speed=0.3 cm/sec.
Figure 6B:
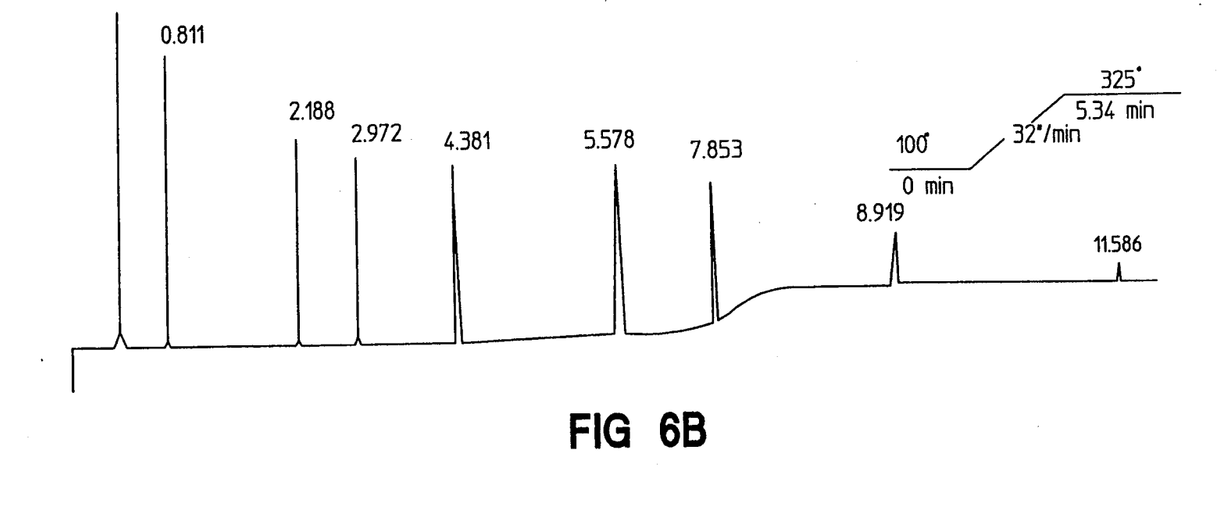
FIG. 6B illustrates the chromatographic output of a gas chromatograph, which employs "new" translated column parameters and new operating parameters 25 psig $H_2$, $u_o$=100 cm/sec, u=50 cm/sec, 0.1 ul split 400:1, chartspeed=0.8 cm/min.

Because of gas compressibility, flow or linear velocity differs at every point along the column, being lower at the inlet or high pressure end and higher at the outlet or low pressure end. The effect of compressibility is reflected in the value for average linear velocity and outlet velocity. Average velocity is used to calculate the holdup time ($t_m$) which is the time required for an unretained substance to travel from inlet to outlet. For constant resolution, the ratio of hold up times over the phase ratio for two columns of different size determines the new oven temperature program required for equivalent separations As illustrated in FIG. 5, column translation is obtained by utilizing the ratio of the new column and the existing column parameters to obtain new operating parameters. If only some of the operating parameters are changed, and if the column parameters do not change, then the ratio of the existing operating parameters and the new operating parameters can be employed to ascertain the unknown operating parameters. In the preferred embodiment, the column outlet linear velocity ($u_{out}$) is employed and greatly simplifies the translation calculations. If column parameters do not change then the only variables available to the user are inlet pressure (Pi) and oven temperature program ramp rate. In order to preserve the order of elution, we change the outlet velocity (increase it) by some factor (3X is reasonable) and proceed to calculate the new Pi and new oven program. It is possible to deliberately sacrifice resolution for speed, without changing the relative order of elution or the elution temperature of the sample components. This is an excellent way for a user to increase analysis speed in a systematic way when the components of interest are well resolved from one another.

The following examples highlight the inventive method and apparatus in which existing column and operating parameters of a known chromatographic method are employed for translating new operating parameters when a new column having new column parameters is installed. The column parameters are first stored in system software associated with the gas chromatograph and used for translating a new set of operating parameters which will provide an identical chromatographic output. In particular, the invention provides for the translation of chromatographic methods to enable the prediction of retention time and peak width values between an existing column and a new column as well as the preservation of peak elution temperature. Example 1, illustrates the calculations required to perform a translation from a first column having a diameter $d_1$ to a second column having a diameter $d_2$. In Example 2, columns having the same column parameters are employed but the linear outlet velocity (an operating parameter) is changed and new inlet pressures and oven programs are calculated to provide the necessary translation. A sample volume -calculation, or a determination of how much sample needs to be injected, is required in most method translations, and is illustrated in Example 3.

Example 1: Column diameters are different

The linear velocity is inversely proportional to diameter and therefore, $r_{uo} = 1/r_d$. Additionally, the liquid phase type does not change.

The previously defined parameters for Column 1 provide for the calculation of the required operational parameters for column 2. In particular, almost all parameters are considered as their ratios between the two columns:

$$r_x = \frac{x_2}{x_1} = \frac{\text{parameter } x \text{ for column 2}}{\text{parameter } x \text{ for column 1}}$$

e.g.

$$r_l = \frac{l_2}{l_1} = \frac{\text{length col 2}}{\text{length col 1}}$$

Thus, the following parameters need to be calculated:
- $r_d$ = diameter ratio = $d_2/d_1$
- $r_l$ = length ratio = $l_2/l_1$
- $r_{df}$ = film thickness ratio = $d_{f2}/d_{f1}$
- $r_\beta$ = phase ratio = $r_d/r_{df}$ If constant resolution is required, then the following must be true:
- $r_d = r_l = r_{df}$
- $r_\beta = 1 = r_R$ The parameters for column 2 are calculated as follows:

$$r_p = \frac{r_\eta r_l r_{uo}}{r_d^2} = \frac{r_l}{r_d^3} \quad \text{for constant resolution and same carrier gas}$$

$$P_{i2} = \sqrt{r_p (P_{i1}^2 - P_o^2) + P_o^2}$$

$$r_j = \frac{(\overline{P_2}^2 - 1)(\overline{P_1}^3 - 1)}{(\overline{P_2}^3 - 1)(\overline{P_1}^2 - 1)}$$

where $$\overline{P} = \frac{P_i}{P_o}$$

$$r_t = \text{ratio of holdup times} = \frac{r_l}{r_j r_{uo}} \quad \frac{r_d r_l}{r_j}$$

for $$r_\beta = 1$$

The reciprocal of $r_t$ is the speed gain or loss factor obtained when translating from column 1 to column 2. For the new column 2 oven program conditions:
(Initial, intermediate, final hold times)$_2$ = (initial, intermediate, final hold times)$_1$ $r_t$
(oven ramp rates)$_2$ = (oven ramp rates)$_1/r_t$ $r_t$ may be viewed as the holdup time ratio or ratio of unretained peak times on the two columns. For example, if $r_t = \frac{1}{2}$, then an unretained peak exits column 2 in half the time for column 1. If all the other peaks in the chromatogram are to elute correspondingly in half the time, the oven program for column 2 has to be twice as fast as column 1. This can be accomplished by shortening holdup times by $\frac{1}{2}$ and increasing rates by two times. In particular, the program on column 2 must execute in half the time of column 1. Therefore, each of the peaks on column 2 will elute with $\frac{1}{2}$ the retention time of column 1. For the special case of constant resolution described in this Example, the peak widths on column 2 will also be $\frac{1}{2}$ those on column 1.

If $r_d \neq r_l \neq r_{df}$ & $r_\beta \neq 1$, ie. general case, then even though $r_t$ will correctly reflect the ratio of holdup times for the two columns, it will not provide the correct multiplier for oven program translation or for calculation of new retention times for retained peaks. The required expression is:

$$r_{tr}' = \frac{r_t}{r_\beta} = \frac{t_{r2}'}{t_{r1}'}$$

$$t_{r2}' = \frac{r_t}{r_\beta} t_{r1}'$$

where $t'_{r1}$ = corrected retention time of peak on column 1 = $t_{r1} - t_{m1}$ $t_{m1}$ = holdup time for column 1

Instead of multiplying oven program hold times and dividing ramp rates by $r_t$, this case requires correction for $t_{m1}$ before multiplication and division respectively by $r_t/r_\beta$.

Example 2: Column 2 Parameters=Column 1 Parameters

In this example, the user wishes to modify the analysis speed, perhaps on the same column, by increasing outlet linear velocity ($u_o$) by, for example, three times. The changes in linear velocity will cause changes in holdup times and necessitate changes in oven program rates and holdup times. Since many analyses have more resolution than needed, the user can thus trade resolution for speed while preserving the elution temperature.

For purposes of this example, a single 200 um column is employed. The outlet velocity $u_o$ is the "new" operating parameter which is "given" in this example and is increased from 50 to 150 cm/sec. The invention then contemplates that the inlet pressures and oven programs are adjusted to match as set forth below:

$$P_{i2} = \sqrt{r_p(P_{i1}^2 - P_o^2) + P_o^2}$$

The oven program correction factor is calculated as:

$$r_t = \frac{1}{r_j r_{uo}}$$

and the speed gain is $1/r_t$.

Step 1 calculate new $P_i$ required to increase $u_o$ 3X
Step 2 calculate $t_m$ and $r_{tm}$
Step 3 calculate new oven program using $r_t$
Step 4 store new setpoints in GC The result will be a runtime that is faster by $1/r_t$ times, but with the same relative order of elution and same temperature of elution for the sample components. This will have broader peaks, hence less resolution than initially because we have deliberately traded resolution for speed.

Example 3: Sample Capacity

Anytime the column size is changed, it is important to determine proportionally, how much sample can be injected without exceeding the capacity of the liquid phase. Now that operational parameters for the column, inlet pressure and oven have been calculated, the sample capacity, or amount of sample required, must be determined. The sample capacity is directly proportional to the relative amounts of liquid phase in the two columns. The sample volume ($r_v$) ratio for the two columns is determined by:

$r_v = r_d r_{d'} r_1$
or volume injected on column 2 is
$V_2 = v_1 r_d r_{d'} r_1$
For example, if $v_1 = 1\mu$ split 100:1
and $r_d = r_{d'} = r_1 = \frac{1}{2}$
then $v_2 = v_1/8 =$
  1 $\mu$l split 800:1
  0.5 $\mu$l split 400:1
  0.1 $\mu$l split 80:1

Which combination of sample size/split ratio can be used depends on the maximum flow available from the split vent and the fraction of the column capacity which remains. In this case, the user most likely would have only the last two options available. The first option, most likely, would require a higher split vent flow than available at the instrument. In our case the instrument would choose the best option (#2) and automatically configure the injector and the split vent flow to achieve the desired split ratio.

Accordingly, it is intended by the appended claims to cover all modifications of the invention which fall within the true spirit and scope of the invention.

Thus, an analyst can choose the appropriate size column, to determine an analysis time and sample size requirements which are optimum for a specific application. The system software can be used to automatically calculate and load setpoints for optimum $U_{out}$ or multiples thereof.

We claim:

1. A computer-based method of controlling a gas chromatograph running system software to produce a new chromatographic output by automatically reconfiguring existing operating parameters of the gas chromatograph in response to the input of new column parameters and a new column, said new chromatographic output being substantially equivalent to a known chromatographic output of a known chromatographic method having both existing column parameters and existing operating parameters, comprising the steps of:
    storing existing column parameters and existing operating parameters of the known chromatographic method on the system software; and
    storing known translation equations on the system software, said translation equations being based on the ratio of new column parameters to existing column parameters; and
    inputting new column parameters corresponding to said new column into the system software; and
    calculating the ratios between new column parameters and existing column parameters; and
    calculating new operating parameters based on the ratios between new column parameters and existing column parameters; and
    automatically reconfiguring the existing operating parameters of said gas chromatograph with said new operating parameters; and
    injecting a sample into said gas chromatograph for chromatographic separation into components, said components being outputted serially from said gas chromatograph; and
    generating an electrical signal corresponding to the serially outputted components; and
    displaying said electrical signal, said signal being the new chromatographic output of said gas chromatograph with said new column and new operating parameters, said new chromatographic output being substantially the same as said existing chromatographic output of said gas chromatograph with said existing column parameters and existing operating parameters.

2. The method of automatically reconfiguring a gas chromatograph as in claim 1, wherein one of said existing operating parameters is the column outlet linear velocity ($u_{out}$).

3. The method of automatically reconfiguring a gas chromatograph as in claim 1, said step of storing existing column parameters further comprises the step of storing the phase ratio of the stationary phase, wherein, the phase ratio of the new column is the same as the old column.

4. The method of automatically reconfiguring a gas chromatograph as in claim 1, wherein the column temperature at which a given chromatographic peak exits the new column is substantially the same as the temperature said peak exits the existing column.

5. The method of automatically reconfiguring a gas chromatograph as claimed in claim 1, wherein said step of automatically configuring the gas chromatograph further comprises the step of adjusting integrator chart speeds to affect registration between output peaks and proportional peak widths between new and existing chromatographic outputs.

* * * * *